United States Patent [19]

Cohn et al.

[11] Patent Number: 4,678,214
[45] Date of Patent: Jul. 7, 1987

[54] SURGICAL CASE CART

[75] Inventors: Robert J. Cohn, Dallas, Pa.; Frank C. Olsson, East Lyme, Conn.; James W. Holzman, New Tripoli; Paul Santarelli, Hudson, both of Pa.

[73] Assignee: Metropolitan Wire Corporation, Wilkes-Barre, Pa.

[21] Appl. No.: 752,099

[22] Filed: Jul. 5, 1985

Related U.S. Application Data

[62] Division of Ser. No. 354,762, Mar. 4, 1982, Pat. No. 4,550,956.

[51] Int. Cl.[4] .................................................. E05C 3/10
[52] U.S. Cl. ................................... 292/213; 312/250; 292/204; 292/DIG. 21
[58] Field of Search ....... 292/213, 204, 218, DIG. 21, 292/241; 312/250

[56] References Cited

U.S. PATENT DOCUMENTS

| | | | |
|---|---|---|---|
| 442,739 | 12/1890 | Shouler | 292/DIG. 21 X |
| 1,061,283 | 5/1913 | Griffin | 292/204 |
| 1,494,512 | 5/1924 | Steiner | 292/202 X |
| 1,878,544 | 9/1932 | Schmidt | 292/202 X |
| 4,073,556 | 2/1978 | Wilson, Jr. | 312/250 |

Primary Examiner—Richard E. Moore
Attorney, Agent, or Firm—Goodman & Teitelbaum

[57] ABSTRACT

A surgical case cart having a closed container supported on a chassis. The closed container includes a pair of front door panels hinged to side door panels which in turn are hinged to side wall sections, so that the container can be completely opened with the front and portions of the sides being exposed by the door panels wrapping around the side and back. The door panels are formed of single pan construction so as to avoid cracks and crevices, and yet exhibit rigidity of a double pan door construction. The lower edges of the door panels provide a baffle effect to reduce the movement of contaminated air into the cart. The top of the cart contains an overhang lip to prevent liquids from spilling into the container. Stem mounted casters are utilized to avoid flat horizontal surfaces on which dirt can collect. The intersection between the back, sides and chassis is constructed to avoid the possibility of collecting contamination and bacteria. A door latch is provided which indicates whether the contents of the cart are sterile or contaminated. Opening of the cart door panels nevertheless can be accomplished without the use of the operator's hands. The cart construction therefore provides improved sterility, greater accessibility, and brings about easier maintenance.

4 Claims, 24 Drawing Figures

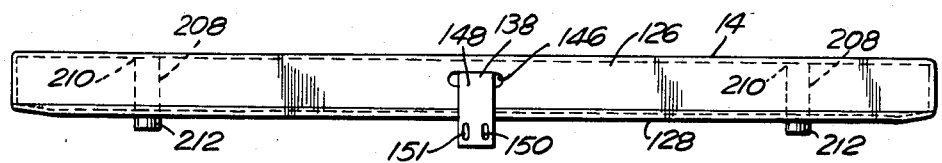
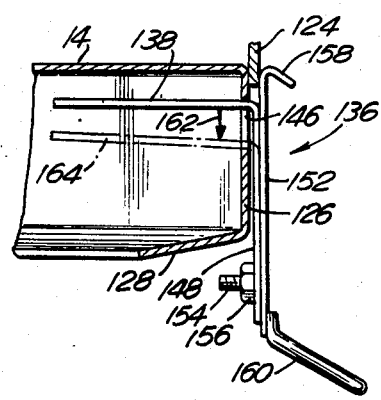
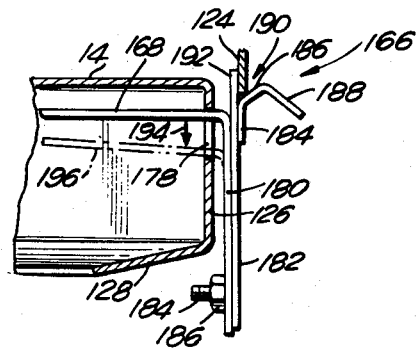
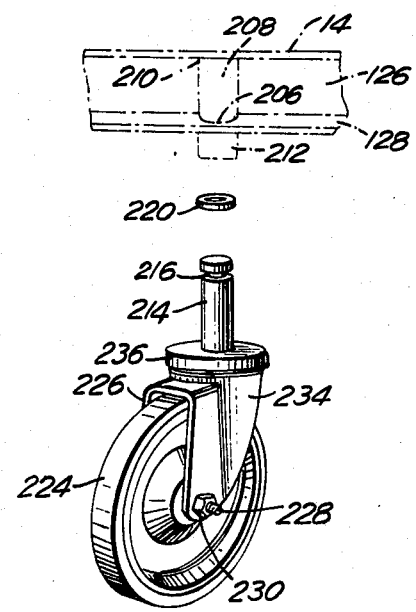
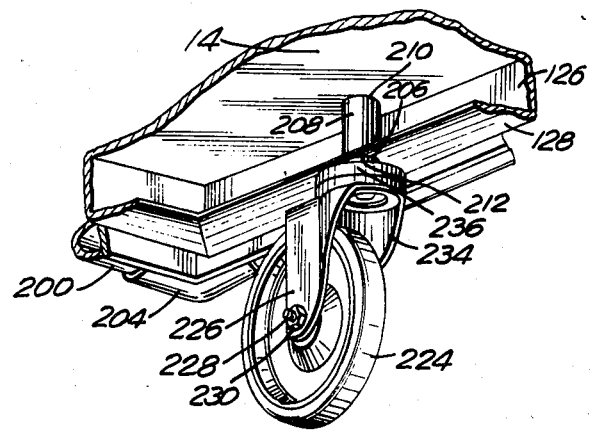

SURGICAL CASE CART

This is a division of application Ser. No. 354,762, filed Mar. 4, 1982, now U.S. Pat. No. 4,550,956.

BACKGROUND OF THE INVENTION

This invention relates to containers, and more particularly to a closed surgical case cart.

Surgical carts are generally used in transporting sterile supplies and devices from a supply room to an operating room, and to transport the soiled equipment from the operating room at the conclusion of the surgery. The particular supplies and instruments are usually stored in a central supply area in a sterilized condition. Prior to the operation, the surgeon determines the particular supplies, instruments, kits, etc. that will be required, and orders these from the central supply area. The materials are collected from the inventory and placed in a surgical case cart and the cart is identified for the particular operation.

When the cart arrives at the operating room area, an inventory is taken of all of the materials to insure that the required equipment is available. Prior to the operation, the cart is wheeled into the operating room and opened. Sterile drapes are used to cover the carts, and the equipment is unwrapped and laid out on the cart top for further use.

When the operation is completed, the used and soiled instruments, and sometimes even the pathological waste, are placed in the cart and the cart is returned to the decontamination area. The cart is then emptied and the instruments are sterilized. The cart is cleaned by placing it in an automated cart wash. The cart is then returned to the central supply area and the cycle repeats.

When the supply room is close to the operating room, a simple, open utility cart may be used to transport the equipment between the supply room and the operating room. These open carts are generally ideal for use since they are open for easy visibility and ready accessibility to the instruments.

However, when the supply room is located at a distance remote from the operating room, the open utility carts are inadequate because they allow contamination of the equipment during transportation through the hospital. As a result, closed carts are employed for such purposes. However, while the closed carts offer improved protection and sterility, they lack the benefits of accessibility and visability offered by the open carts.

Many prior art closed carts have been provided. While these have satisfied the general purpose of transportation to and from the operating room, they have been inconvenient since it is awkward to gain access to the interior of such closed carts during the course of the operating procedure.

Additionally, a great problem with prior art closed carts concerns the ability to clean and sanitize the cart. Many of the carts include crevices and corners resulting from particular construction which makes it difficult to completely clean out the carts. As a result, residual bacteria often remains on such prior art carts. Furthermore, in many cases where horizontal areas are provided in the cart construction, water from the automatic wash can become entrapped in such areas and will continuously drip wash water from these areas.

A further problem with prior art carts concerns the possibility of contamination entering into the cart. Typically, liquid spilled on the cart top can find its way inside of the doors of the cart. Should liquid be accidentally spilled onto the cart, although someone will wipe and sanitize the exterior, it is unlikely that he would realize that the interior has also become contaminated due to the leakage into the cart. As a result, it is possible for contaminated instruments to be used during actual surgery.

Since the cart is used both to bring sterile instruments into the operating room, as well as to remove contaminated instruments from the operating room, it is advisable to have an indication on the cart whether the particular closed cart contains sterile instruments or contaminated instruments. Should no indication be provided, it is possible that a contaminated cart would be opened in a sterile area, and the reverse could also occur.

Other problems with prior art carts concern their particular types of construction. For example, many closed carts use a double pan door. While such doors provide rigidity, contamination may remain within the space between the door walls. Alternately, the water from the automatic wash can become entrapped in this space. The connection of the wheels or casters to the chassis of the cart can provide horizontal areas having cracks and crevices therein which can store bacteria and other contamination. The interconnection between the walls of the cart can also provide areas and crevices for contamination.

Accordingly, although numerous surgical case carts are readily available, there appears to be needed an improved cart which avoids the aforementioned problems.

SUMMARY OF THE INVENTION

Accordingly, it is an object of the present invention to provide a surgical case cart which is closed and yet provides the benefits of an open cart.

A further object of the present invention is to provide a closed surgical case cart which has increased visability and accessibility through the use of side doors as well as front doors.

Another object of the present invention is to provide an improved closed surgical case cart having minimal cracks, crevices, or concealed areas, thereby avoiding the storage of bacteria and preventing the entrapment of wash water.

Still another object of the present invention is to provide a closed surgical case cart permitting increased accessibility, while facilitating and improving the cleaning aspects of the cart.

A further object of the present invention is to provide a closed surgical case cart having a chassis with an improved mounting of the casters to avoid flat horizontal surfaces on which dirt can collect.

Another object of the present invention is to provide a closed surgical case cart having a selected relationship between the panels and walls of the cart so as to improve the sanitary nature of the cart.

Another object of the present invention is to provide a closed surgical case cart having single pan doors with improved rigidity so as to avoid entrapment of contamination or wash water within the doors.

A further object of the present invention is to provide a closed surgical case cart having a surface structure whereby liquids spilled on the top of the cart do not drip into the cart, but are rather dripped onto the outer surface of the cart.

Yet a further object of the present invention is to provide a closed surgical case cart having doors which create a baffle effect, thereby reducing the movement of contaminated air into or out of the carts.

Still another object of the present invention is to provide a closed surgical case cart having a door latch providing an indication of whether the contents of the cart are sterile or contaminated.

Yet a further object of the present invention is to provide a closed surgical case cart wherein the doors can be easily opened without the use of the operator's hands.

Briefly, in accordance with the present invention, there is provided a closed surgical case cart having a container portion including a base, a top wall, a rear wall, opposing side walls, and a front wall. The front wall is split or divided so as to define a pair of adjacent front door panels. Each of the side walls are also split or divided, wherein the forward portion thereof defines a side door panel and the rearward portion thereof defines a fixed side panel. Hinges are provided for coupling the front door panel to a respective side door penel. The side door panels in turn are hinged to a respective fixed side panel. In this manner, the container portion can be maintained in a closed condition or in an open condition. In the open condition, the entire front and part of the sides of the container portion are opened to provide improved visability and access to the interior of the container portion.

In an embodiment of the present invention, when in an open condition, the side door panels overlie the fixed side panels and the front door panels overlie the back wall, so as to have the doors completely surround the container portion, whereby only interior surfaces are exposed.

The side door panels are released by means of a latch. With the latch secured in the side door panels, the front door panels can be folded onto the side walls, thereby providing a partially opened condition. An arm is provided for spacing the front door panels from the fixed side panels when the container is in an open condition with the side door panels released, to thereby expose all of the surfaces of the front and side walls to facilitating washing of the cart.

The present invention further contemplates a surgical case cart comprising an enclosed container having a pair of adjacent front door panels with an overlying top wall. A latching mechanism is provided which has two distinguishably different closed positions for locking the door panels into a closed condition. It also has an open condition for permitting opening of the door panels. Accordingly, one of the two closed positions provides an indication that the contents of the carts are sterile and the cart is therefore available for surgery. The other of the closed positions provides an indication that the contents are contaminated and that the cart is now ready for transport to the decontamination area.

In an embodiment of the present invention, there is also provided a foot latch so that when the latching mechanism is in its open position, the door is easily released by means of the foot latch without the need of utilizing the operator's hands to open the door. The foot latch is inoperative when the latching mechanism is in either of the above mentioned two closed positions.

The present invention further contemplates a surgical case cart having an enclosed container with a front door panel having an outer surface, the container having an overlying top wall. The top wall has at its forward end a downwardly depending lip. The distal end of the lip terminates at a location slightly above and forward of the outer surface of the front door panel. In this way, liquid spilled onto the top wall can roll down the lip and drip from its edge onto the outer surface of the front door panel, and will not drip into the inside of the container. The front door panel itself can be restrained by means of a stop flange which has a first portion thereof downwardly sloping from the lip, and a second portion thereof extending vertically downward to serve as the door stop.

The present invention also contemplates a surgical case cart having an enclosed container supported by a chassis. The chassis includes a base wall with a downwardly depending skirt peripherally formed thereabout, and an inwardly turned flange at the lower edge of the peripheral skirt. A number of sockets are securely fastened into the flange. A stem mounted swivel caster is secured in each socket. In this way, there are no horizontal surfaces or fastening members which can store bacteria or retain liquid from the wash water.

The cart can include door panels having a single pan construction with stiffening wires formed internally of the door panels for increased rigidity of the door panels. The stiffening wires effectively replace the second pan to effectively provide the equivalent of a double pan door, while avoiding the spacing between two sheets of door material. The stiffening wires can typically be an intersecting X-shaped wire configuration.

In order to avoid the cracks and crevices typically found in such prior art carts, the container can include a structure which avoids any vertical abutment between the container portion and the chassis portion. For example, the lower edge of the back wall and side walls of the container portion can have an inwardly sloping flanged edge which contacts the base wall of the chassis at a location spaced from the peripheral edge of the base wall. Suitable fastening devices can be provided for coupling the flanged edge to the base wall. An alternative structure would be to provide the back wall and the base wall of integral construction, thereby avoiding any seams or crevices at that back junction.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which:

FIG. 9 is a front elevational view of the bottom chassis of the cart;

FIG. 10 is a fragmented sectional elevational view showing the pedal operated front door cam latch;

FIG. 11 is a fragmented sectional elevational view of the rear cam latch;

FIG. 12 is an exploded perspective view of the caster assembly;

FIG. 13 is a fragmented perspective view of a bottom corner of the surgical case cart, showing the caster positioned in the bottom chassis;

In the various figures of the drawing, like reference characters designate like parts.

DESCRIPTION OF THE PREFERRED EMBODIMENTS

Figure 1:
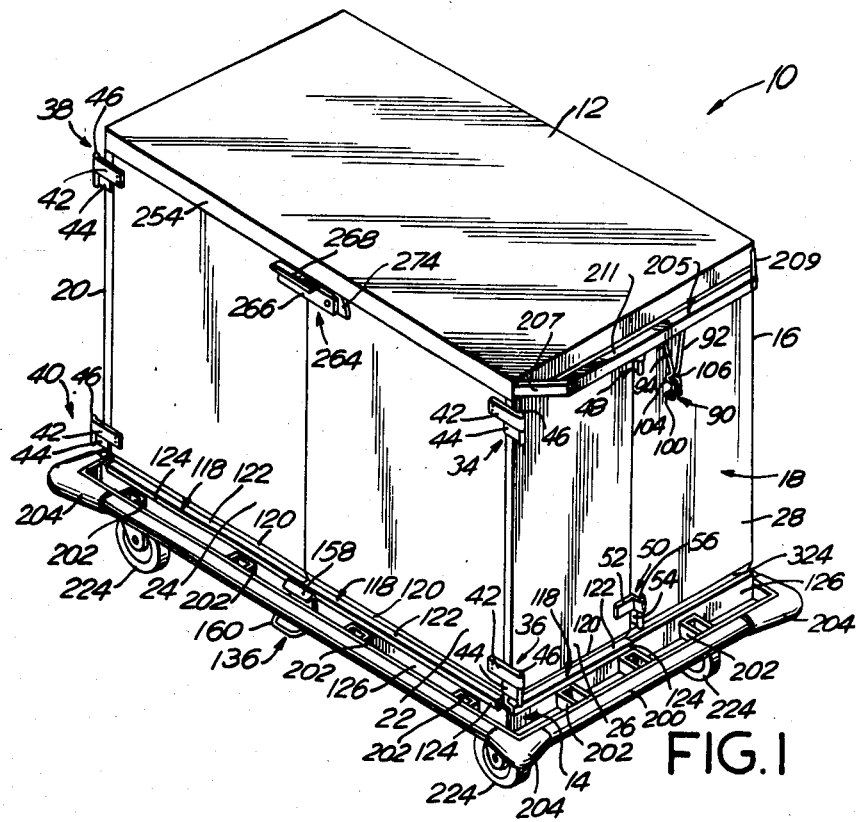
FIG. 1 is a perspective view of a surgical case cart according to the present inventions, showing a closed condition thereof.
Figure 2:
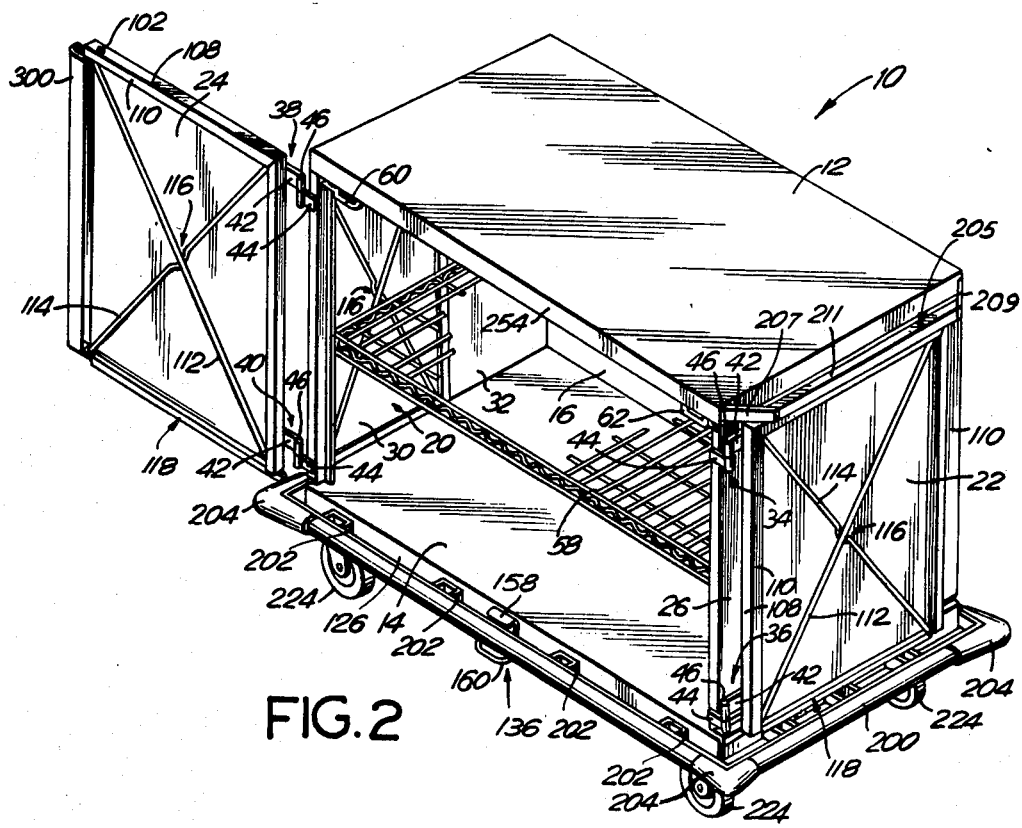
FIG. 2 is a perspective view of the surgical case cart showing the front door panels opened.

Referring now to FIGS. 1 and 2, the surgical case cart of the present invention is shown generally at 10 as comprising a closed container including a top wall 12, a bottom wall 14, a rear wall 16, side walls 18 and 20, and adjacent front door panels 22 and 24.

The side wall 18 is split or divided, the forward portion thereof defining a side door panel 26, and the rear portion thereof defining a fixed side wall 28. Similarly, the side wall 20 is split or divided to define the side door panel 30 at the forward portion thereof and the fixed wall 32 at the rear portion thereof.

The front door panel 22 is coupled to the side door panel 26 by means of the split hinges 34, 36. Similarly the front door panel 24 is coupled to the side door panel 30 by means of the split hinges 38, 40. Each of the split hinges 34-40 includes an upper plate 42 coupled to the outer surface of the respective front door panel by means of rivets, or other suitable fastening members, and a lower plate 44 coupled to the respective jamb of the side door panels. The two hinge plates 42, 44 are held together by a hinge pin 46. Each of the split hinges 34-40 permits approximately 270 degrees of rotation, whereby the front door panels 22, 24 can be opened up and swung around to overlie the side walls 18, 20. As shown in FIG. 2, the front door panel 22 is swung completely around so as to overlie such side wall 18.

The side door panel 26 is hinged to the fixed side wall 28 by means of the hinges 48, 50. The opposing side door panel 30 is similarly hinged to the fixed side wall 32. The hinges 48, 50 include an upper plate 52 connected to the outer surface of the respective side door panel, and the lower hinge plate 54 connected to the jamb of the respective fixed side wall. The two hinge plates 52, 54 are held together by means of a hinge pin 56.

Figure 5:
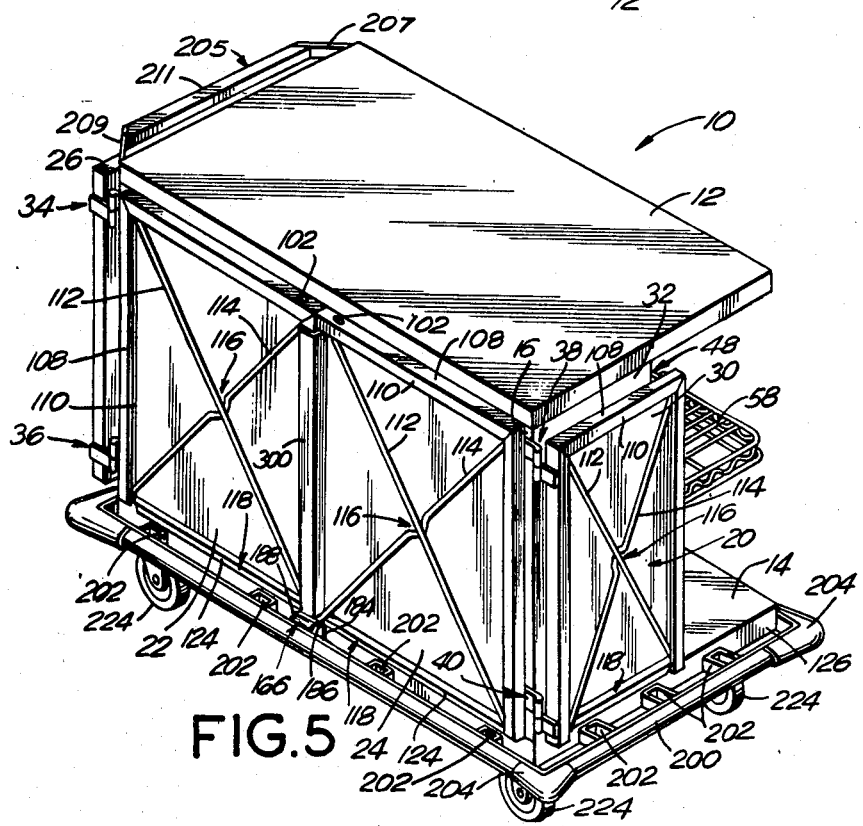
FIG. 5 is a perspective view of the surgical case cart taken from the rear, showing the cart in its completely open condition with both front and side doors opened.

The hinges 48, 50 permit at least 180 degrees of rotation. In this manner, the side door panel 26 can be swung out so as to overlie the adjacent fixed side wall 28. Similarly, on the opposing side, the side door panel 30 could be swung out to overlie the fixed side wall 32. With the side door panels open and overlying its respective fixed side wall, the front door panels can completely swing around so as to overlie the back wall 16, as shown in FIG. 5. With both the front door panels and side door panels opened, the cart 10 is substantially exposed providing good visability to the contents of the cart as well as accessibility to remove items from within the cart. Typically, a shelf 58 is provided inside the cart which can be made as a roll-out shelf to gain further access to the inside of the cart.

As a result of the ability to open the cart into an exposed position as shown in FIG. 5, there results the benefits of both a closed and open cart. On the one hand, the cart itself can be completely closed as shown in FIG. 1 to maintain a sterile and clean condition. At the same time, it can be opened completely into the condition shown in FIG. 5 to gain the accessibility of an open cart. This accessibility is not only for the convenience of removing items from the cart, but also helps to reduce exposure to contamination of the person unloading the contaminated cart. It should be appreciated, that with the doors of the cart completely open, as shown in FIG. 5, the outside surfaces of all of the doors are abutting the outside surfaces of the back wall 16 and the side walls 18, 20. As a result, all of such outside surfaces are substantially shielded from air movement by their juxtaposition. The only surfaces that are exposed are the clean inside surfaces. Thus, even though the cart moves through contaminated areas from the supply room to the operating room, and although the outside surfaces may become somewhat contaminated, in the operating room, these outside surfaces are all shielded and only the sterile inside surfaces of the doors and walls are exposed.

As a result of the particular hinge construction, as described, it should be appreciated that the cart can be opened from the closed condition of FIG. 1 to the open condition of FIG. 5 with only minimal clearance between the cart and any wall behind it. It should also be noted that the cart need not be placed in the fully open condition, as shown in FIG. 5. The cart could be maintained in a partially open condition with only the front door panels open, as shown in FIG. 2.

Figure 3:
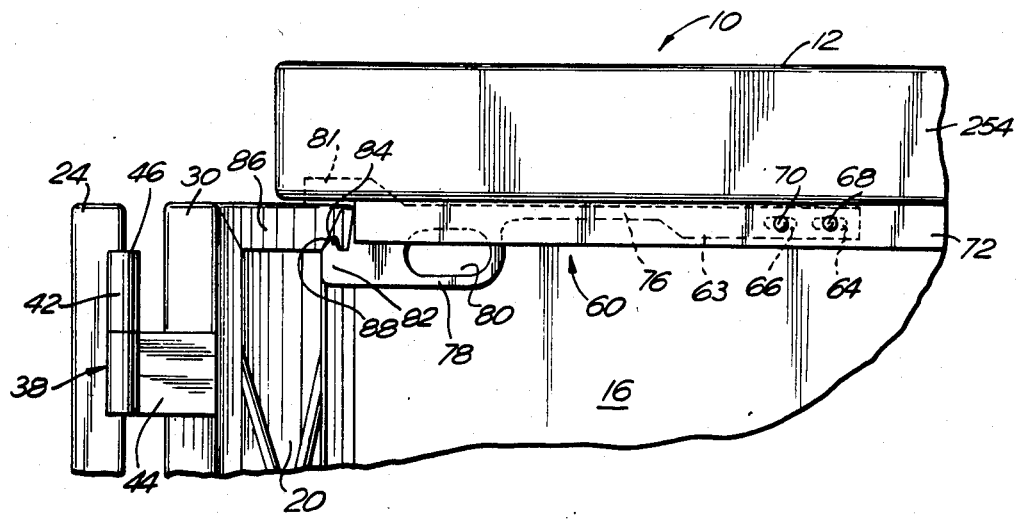
FIG. 3 is a fragmented front view showing the upper ledt hand corner of the surgical case cart with the front door opened and exposing the release latch for the side door panel.
Figure 4:
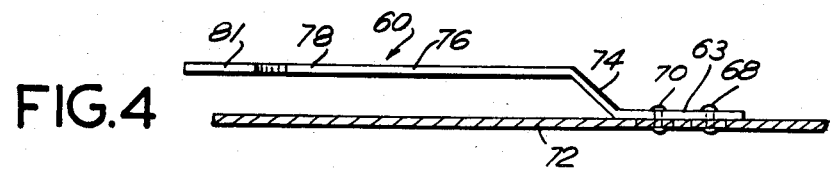
FIG. 4 is a top sectioned view showing the release latch of FIG. 3.

The side door panels 26, 30 can be selectively opened by means of a release handle 60 in the front upper left hand corner, and a release handle 62 in the front upper right hand corner of the cart as shown in FIG. 2. These handles 60, 62 are better shown by way of examples in FIGS. 3 and 4, which show the details of the handle 60. The handle 60 includes an arm 63 having elongated slots 64, 66 at the rear portion to accommodate fastening members 68, 70, typically shown as rivets. The arm 63 is fastened to a downwardly depending lip 72 extending from the top wall member 12.

The arm 63 includes a dog leg offset portion 74 which then continues into a reduced height section 76. The handle then continues in cantelevered fashion to include a grip 78 which contains a cut out portion 80 for gripping the handle 60. At the front end of the handle 60, there is a jaw member including an overlying upper lip 81 and a lower jaw 82. An upwardly extending tooth 84 from the lower jaw 82, serves as a catch for grasping beneath the overhanging flange 86 of the side door panel 30. It should be noted, that the front surface of the tooth 82 has a cam surface 88 permitting a cam latching of the door.

Accordingly, when the side door panel 30 is closed against the latching mechanism of the handle 60, the door panel will ride against the cam surface 88 and will automatically latch closed. In order to release the door panel 30, the grip 78 of the handle 60 is pulled downwardly in order to release the tooth 84 from beneath the flange 86, and the door panel 30 can then be opened. A similar arrangement is provided for the other handle 62 at the front right side which serves to hold the side door panel 26. If it is found that the dog leg offset portion 74 deflects too much, an additional metal stiffener can be added, or the offset can be reduced or eliminated.

Figure 6:
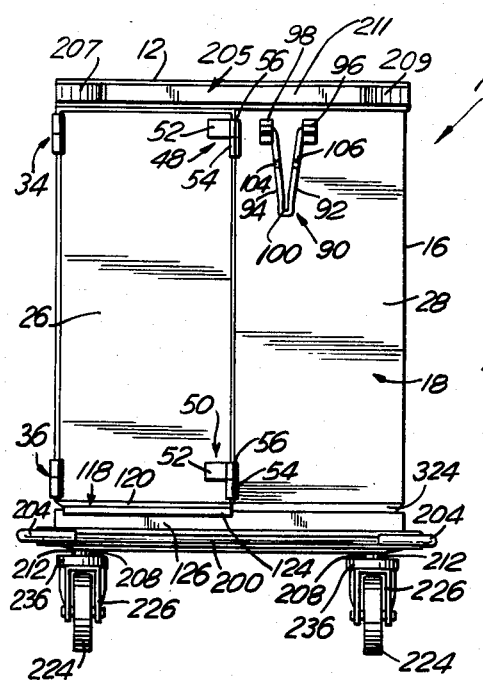
FIG. 6 is a side elevational view of the surgical case cart.
Figure 7:
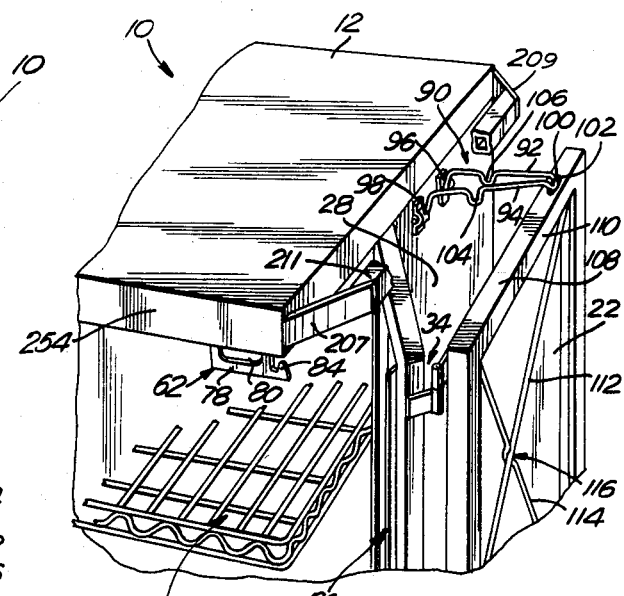
FIG. 7 is a fragmented perspective view showing the upper right hand side of the surgical case cart with the doors in the retained position for washing of the cart.

As can best be seen in FIGS. 1, 6 and 7, connected on each side of the fixed side walls 28 and 32, is a swinging hook arrangement 90. The hook itself is a substantially V-shaped member having opposing side legs 92, 94. The distal ends of the hook are outwardly bent to form feet which are secured to the outer surface of the fixed panels 28, 30 by means of the clamps, 96, 98. The feet are loosely held in the clamps 96, 98 to permit swinging of the hook. In its relaxed position, the hook hangs downwardly as shown in FIGS. 1 and 6. However, the hook can be swung upwardly as shown in FIG. 7. At the apex of the legs 92, 94 is provided a downwardly extending bend to form a finger 100 which can fit within a detent or cut out 102 formed in the upper edge of the door panel 26. A similar detent or cut out 102 is provided in the upper end of the other side door panel 30. U-shaped bends 104, 106 are respectively formed in the legs 94, 92 corresponding to the downward bend of the finger 100 in order to permit the hook to abut against the outer surface of the fixed side walls 28, 32, as shown in FIG. 1.

As shown in FIG. 7, the side door 26 is unlatched by means of releasing the door using the handle 62. The front door panel 22 is swung outwardly and then back to be held in place by means of the outward extending hook arm 90, with the finger 100 entering into the cut out 102. The front door panel 22 is then held in place, being spaced from the fixed side wall 28. At the same time, the side door panel 26 is held opened in an angled position away from the fixed side wall 28. In this position, it should be noted, that all door surfaces including the edges, door jambs, etc. are exposed. Accordingly, during the washing of the cart, and especially when the cart is placed in an automatic cart wash, the hooks 90 are used to hold the door panels in the position shown in FIG. 7. In this position, the entire cart is exposed to the washing action and the cart can be readily cleaned.

In prior art carts, the door panels are typically a double pan door construction. While these types of doors provide rigidity, there is a space between the two layers of material which has a tendency to collect contaminated material, bacteria, etc. Additionally, when placed in a cart wash, some of the wash water can collect in this space and will not drain out. This will also cause contamination. Furthermore, the water will continuously drip out after the cart has been washed and provide a steady drip of wash water.

As seen in the figures, the present door panels are formed of single pan construction with a substantially U-shaped channel about the edge thereof. Specifically, as shown in FIGS. 2 and 5, the door panels 22, 24, 26 and 30 have a single layer of material and at the peripheral edge, there is formed the U-shaped channel having a horizontal flange section 108 with a depending lip 110 at the peripheral edge thereof, the lip 110 being inwardly directed toward the center of door panel. This type of single pan construction with an inwardly directed U-shaped channel about its periphery is also utilized for the base wall 14.

In connection with the side door panels 26, 30 and the front door panels 22, 24, there is provided additional stiffening by means of the stiffening rods 112, 114, which are placed in the form of an intersecting X-shaped configuration. The distal ends of each of the rods are welded to the inside of the U-shaped channels formed about the periphery of the doors. At the center 116, in order to accommodate the criss crossing of the rods, one of the rods can be formed with a U-shaped bend in which the other crossing rod can sit, as best shown in FIG. 7. The two rods are welded together at their intersection 116. The utilization of the intersection rods provides the equivalent of an inner pan to the door panels. However, it also avoids the empty space between the prior art pans which would normally collect contamination. Furthermore, the utilization of the intersecting wires provides exposed surfaces which can be readily cleaned in the automatic cart wash and avoids horizontal surfaces which can be contaminated.

At the lower end of the front door panels 22, 24, as well as the side wall panels 26, 28, there is provided a separate stiffening member 118. Specifically, as shown in the figures, the lower edge of the door panels are inwardly bent in a substantially V-shaped configuration having an initial inward bend 120 followed by a lower outwardly directed bend 122. The bottom portion thus extends downwardly into an overhanging lip 124 which overhangs the periphery 126 of the base wall 14. Such lower edge members 118 provide rigidity to the door. At the same time, they present a baffle against outside air into the container. By forming the lower edge member 118 integrally with the door panel itself, it avoids the attachment of a separate stiffening or baffle piece. Such attachment would result in areas in which bacteria could grow. Utilizing this construction, rigidity is provide as well as an integral baffle, and these benefits are achieved without causing additional sources for contamination.

Figure 8:
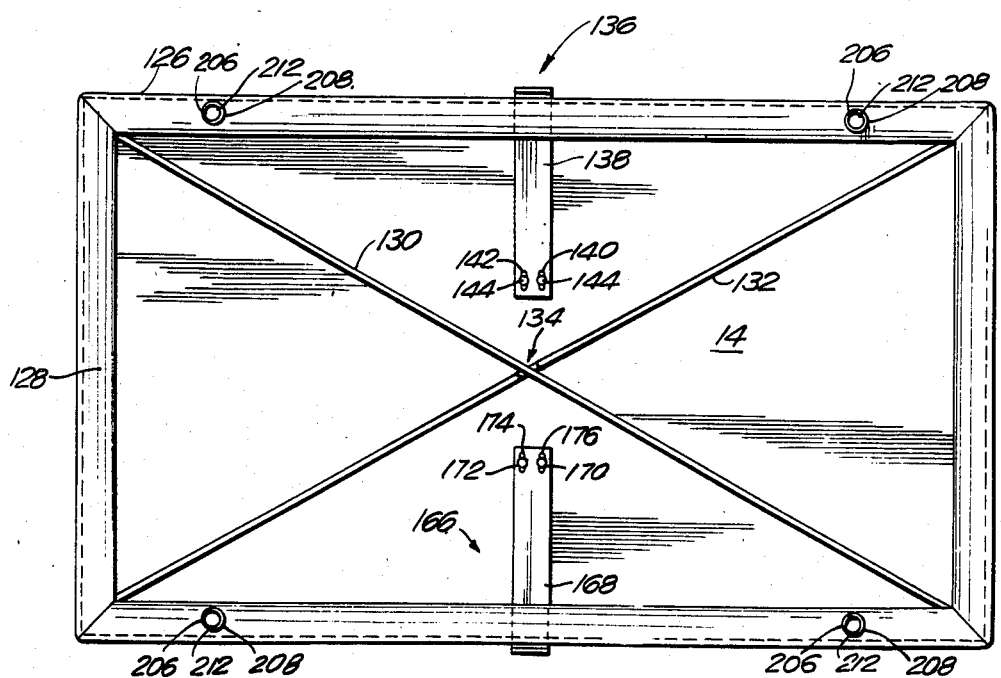
FIG. 8 is a bottom view of the cart with the casters removed.

Referring now to FIGS. 8 and 9, the construction of the base wall 14 is noted to include the downward directed flange or periphery 126 terminating into an inwardly directed flange 128. Again, stiffening members 130, 132 are provided in an intersecting X-shaped configuration with the distal ends of the rods being welded to the inside of the U-shaped channel formed at the periphery of the base member 14. At the center 134, one wire 132 forms a U-shaped bend to permit passage therethrough of the other wire 130. If necessary, suitable spacers can be provided to stand off the wires 130, 132 from the base wall 14.

The front door panels are held in place by means of a foot operated cam latch, shown generally at 136 in FIGS. 1 and 2. This cam latch is shown in more detail in connection with FIGS. 8, 9 and 10. The latch itself, as shown in FIG. 8, includes a cantelevered arm 138 having elongated slots 140, 142 adjacent the distal edge portion thereof through which are placed fasteners 144, such as rivets. The arm 138 extends along the underside of the base wall 14 and passes through a slot 146 provided through the flange 126 formed peripherally about the base wall, as shown in FIGS. 9 and 10. The cantelevered arm 138 after passing through the slot 146 bends downward into a right angle connecting plate portion 148 having elongated slots 150, 151 at the end thereof. Connected to the plate portion 148 is a cam latch plate 152, which is retained in place by means of the bolts 154 and nuts 156, the bolts 154 passing through the elongated slots 150, 151. At the upper end of the latch plate 152, there is provided a downwardly angled finger 158 forming a cam surface therealong. At the lower end of the plate 152, there is connected a U-shaped foot pedal 160, better seen in FIGS. 1 and 2.

The lower edges 124 of the front door panels can be closed by pressing them against the finger 158. The door panels side over the finger 158 depressing the entire mechanism as shown by the arrow 162 in FIG. 10, so that the arm 138 moves downward in the slot 146 to the position shown by the dotted lines 164.

In order to release the door panels, the operator presses his foot down on the foot pedal 160, thereby again lowering the arm 138 to the position shown at 164, whereby the door panels will be released from the latch finger 158. It should be appreciated that the lower edges 124 of the door panels are held securely closed avoiding any contamination which might flow into the container. The front latch 136 is therefore a latch which provides both a cam latch to close the door, and a foot release to open the door.

When the container is opened to its fully opened condition as shown in FIG. 5, the front door panels 22, 24 overlie the back wall 16 and are held in place by an additional latch shown generally at 166, in FIG. 5. This latch 166 is better shown in FIGS. 8 and 11. The latch 166 itself includes a cantelevered arm 168 held in place beneath the base wall 14 by means of fastening members, such as rivets 170, 172 which fit into the elongated slots 174, 176. The arm 168 extends through a slot 178 formed in the back portion of the flange 126 of the base wall 14, and extends downwardly to a connecting plate portion 180. A cam latch plate 182 is connected to the plate portion 180 by means of the bolts 184 and nuts 186. The latch plate 182 includes a finger portion fastened thereto having a connecting section 184 which fastens directly onto the plate 182. An upwardly inclined cam surface 186 extends from the section 184, and continues into the downwardly extending cam surface 188.

The lower edge 124 of the front door panel 24 can latch into the locked position by sliding over the cam surface 188 and resting within the notch 190 defined between the upper edge 192 of the plate 182 and the bottom of the cam surface 186. The door can also be pulled out from its closed position by passing the door edge 124 over the cam surface 186. In each case, the cantelevered arm 168 moves downwardly within the slot 178, as shown by the arrow 194, to the position shown in the dotted line 196. It should therefore be appreciated, that the latch 166 forms a cam in, cam out type of latch.

As shown in FIGS. 1, 2, 5 and 6, there is provided a bumper rail 200 peripherally about the base wall 14. The rail 200 is held in plate by means of U-shaped clamps 202 which are typically bolted onto the flange 126 formed about the base wall 14, and are also bolted to the rail. At each corner of the guard rail 200, there are provided bumper guards 204, typically formed out of rubber-like material. The peripheral size of the guard rail 200 is such that it forms the outermost surface for the cart 10, and accordingly prevents any other portion of the cart from bumping into walls or damaging areas as the cart 10 moves through the hospital.

At one end of the upper wall 12, there is also provided a push/pull hand rail or handle 205. The ends 208, 210 of the hand rail or handle 205 are angled and interconnect to the center hand rail section 211.

Normally, casters are provided on the surgical case cart. The casters are usually of the plate type and are mounted on horizontal members under the chassis by conventional means, such as threaded fasteners. In the prior art carts, these horizontal members are difficult to clean completely and, in some cases, they are designed in such a way that thorough cleaning is virtually impossible and/or in such a way that the cleaning solution becomes entrapped and later drips onto the floor.

Referring now to FIGS. 8, 12 and 13, it will be noted that the underside of the present chassis are free of these horizontal caster supports. Instead, apertures 206 are initially formed in the flange 128 of the base wall 14, generally adjacent the four corners of the cart. Inserted within the apertures 206 are sockets having a tubular portion 208 which extends through the aperture 206 and reaches up to the underside of the base wall 14. It can then be welded in place along the periphery 210 of the tubular junction. Likewise, the interconnection at the aperture 206 can also be welded. The socket 208 includes an exposed portion 212.

The casters themselves are of the stem type comprising a tubular stem 214 having a peripheral groove 216 at the end portion of the stem 214. A spring ring 220 is provided for fitting into the groove 216. With the ring 220 in place, the stem 214 is pressed into the socket 208 and is securely held in place.

The caster itself is of the usual stem type including the wheel 224 secured in a yoke 226 by means of a threaded bolt 228 acting as an axle, and held by means of the nut 230. The yoke 226 forms a housing 234 connected to the ball bearing assembly 236. The stem 214 sits upwardly on the ball bearing assembly 236.

With the construction of the caster assembly as shown, there is avoided the problem of the horizontal members which would serve as a source of contamination entrapment. It should also be noted, that the flanges 128 themselves, are downwardly sloped, as shown in FIGS. 10, 11 and 13. This provides for drainage of fluid from the surface of the flanges 128 so as to permit cleaning of the base wall 14.

Figure 14:
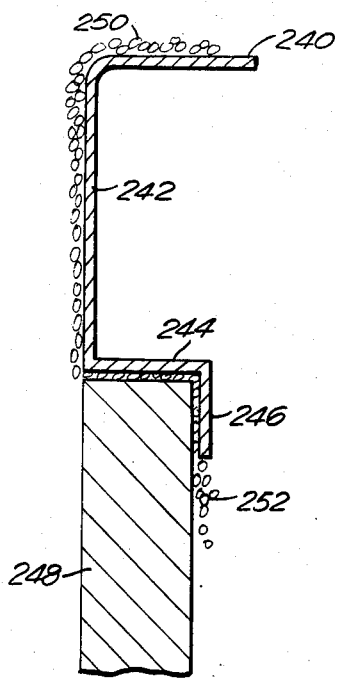
FIG. 14 is a fragmented sectional side view showing the junctional between the front door panel and the top wall in accordance with the prior art surgical case carts.

Referring now to FIG. 14, there will be described an unsanitary condition existing in connection with prior art carts, which is avoided by the construction of the present surgical case cart. Specifically, as shown in FIG. 14, the top wall 240 of prior art carts typically includes a downward depending skirt portion 242 which continues into an integral horizontal section 244 and then into a downward lip 246. The sections 244 and 246 form a seat which receives the conventional door panel 248, and provide a stop for such door panel.

With the construction shown in FIG. 14, if a liquid is spilled onto the top surface 240 of the prior art cart, as shown at 250, the droplets of the spilled liquid will roll off the edge of the cart and run along the skirt portion 242. However, these droplets tend to adhere to the metal surface as a result of surface tension. These droplets will therefore run along the horizontal surface 244, and then run down along the vertical lip 246. As a result, it can drip off that vertical lip, as shown at 252. However, this construction permits the liquid to enter the interior of the container, and contaminate same.

Accordingly, if liquids are accidentally spilled onto the prior art cart surface 240, and if the cart is ready for use, someone will generally wipe and chemically sanitize the exterior of the cart. However, it is unlikely that the individual will realize that the interior is also contaminated. As a result, when using the prior art cart, it is possible for contaminated instruments to be used in surgery.

Figure 15:
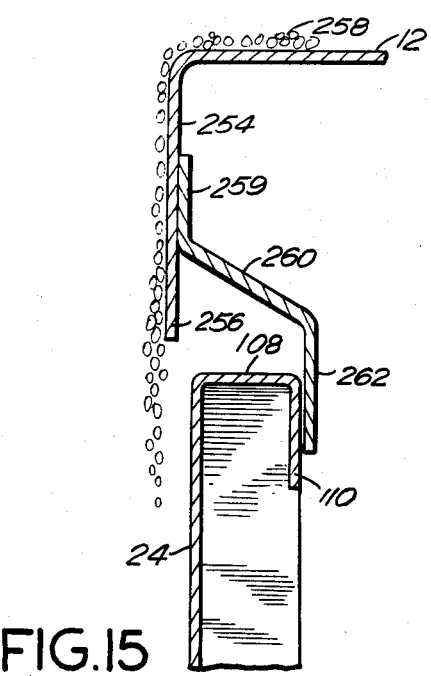
FIG. 15 is a fragmented sectional view similar to that shown in FIG. 14, showing the novel arrangement between the front door and the top wall of the surgical case cart of the present invention.

Referring now to FIG. 15, it will be noted that the construction of the present surgical case cart avoids this above-mentioned contamination problem. Specifically, the top wall 12 also includes a downwardly depending skirt portion 254. However, the skirt portion 254 terminates in a free distal edge 256. As a result, fluid 258 which may spill onto the surface of top wall 12 will run along the skirt portion 254. However, once it reaches the free end 256, it will drop down outside of the cart. It should be noted, that the distal edge 256 terminates at a point above and slightly outward of the door panels, such as the door panel 24, as shown. As a result, there is no possibility of this liquid 258 flowing onto the container itself.

The present construction also eliminates the horizontal dirt catching ledge 244 above the door panel 248 as in the prior art shown in FIG. 14. Instead, a separate retaining member is connected to the inner surface of the skirt portion 254 by means of the connecting section 259, which continues into the downward sloping section 260, terminating in the lip 263. The door panel is retained by means of the lip 262 holding it in place. Thus, the prior art horizontal section 244 has been eliminated and replaced by the sloping section 260 of the present invention, which is preferable since water can now drip off this sloping ledge during the cleaning thereof, and no dirt catching pockets or horizontal surfaces are available for contamination.

Although the front door panels 22, 24 are held in place by means of the foot release latch 136 heretofore described, a locking mechanism is also required so that the foot pedal will only operate when the door panels are unlocked. Such locking mechanism is shown in detail in FIGS. 16-18. Additionally, most prior art carts include a locking mechanism which has only two positions indicating whether the door is locked or opened. However, it is now appreciated that there are two occasions for the door panels to be locked.

Specifically, initially when the sterile instruments are placed in the container, it is locked and ready for transport into the operating room. After the contaminated instruments have been placed into the cart, it is again locked for transporting back to the decontamination area. It would be preferrable to have an indication of when the door panels are locked with sterile instruments, and when the door panels are locked with contaminated instruments. By having a locked position unique for sterile instruments, there is avoided the possibility of having the contaminated instruments brought back into the operating room. Also, by providing an indication that the door panels are locked with sterile instruments, it would avoid the possibility that a sterile cart ready for operation will be sent to the decontamination area.

Figures 16, 17, 18:
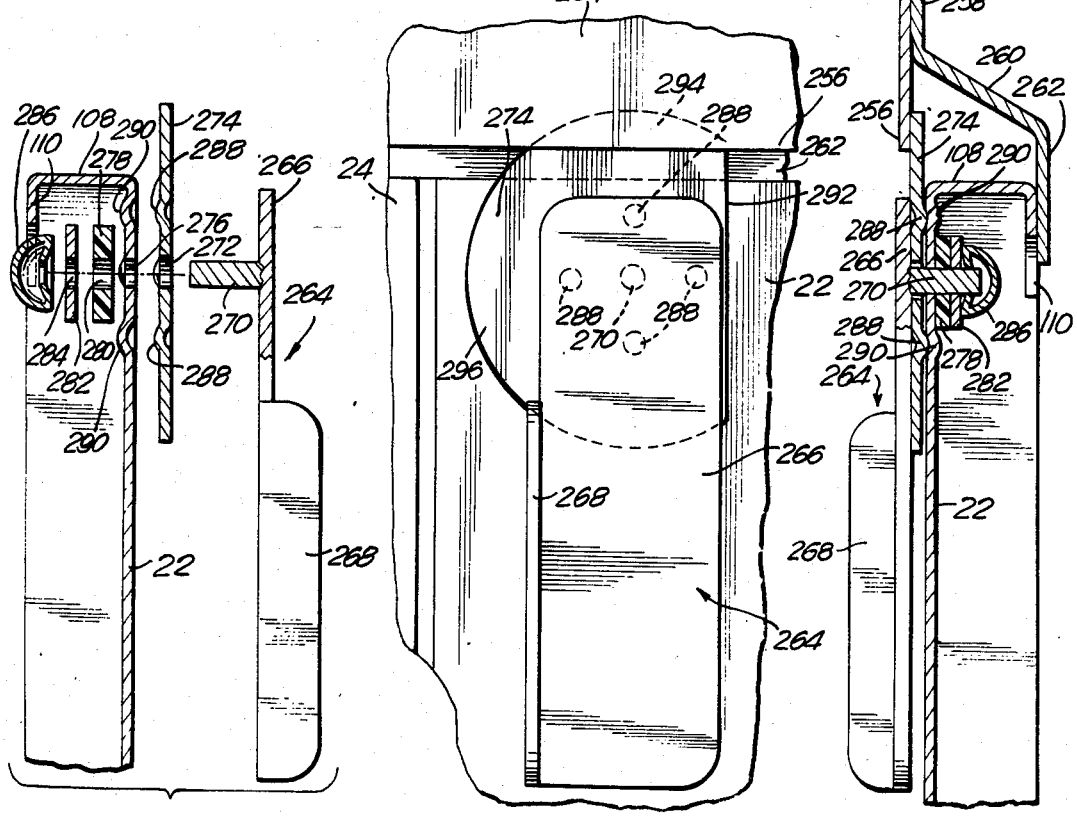
FIG. 16 is an exploded sectional elevational view showing the three position latching mechanism.
FIG. 17 is a fragmented front view of the latching mechanism shown in one of its locked positions.
FIG. 18 is a fragmented sectional view showing the assembled latching mechanism of FIGS. 16 and 17.

As shown in FIGS. 16-18, the locking mechanism includes a handle portion 264 having a flattened plate 266 which rests against the outer surface of the door panel 22 and a perpendicular handle section 268 for manipulation of the locking mechanism. The handle section 268 extends only partially along the edge of plate 266. Connected to the plate 266 is a post 270 which passes through an opening 272 in a latch plate 274, and continues into an opening 276 provided in the front door panel 22. The post 270 is secured in place by means of a compression washer 278 having an aperture 280 therein and a steel washer 282 also having a corresponding aperture 284 therein. The post 270 is secured in place by means of the push-on cap nut 286.

The latch plate 274 is welded to the plate 266 for rotation therewith. The latch plate 274 includes a plurality of nipples or protusions 288. These nipples 288 are received in detents 290 formed directly into the wall of the door panel 22. As shown, there are a total of 4 detents 290 and corresponding nipples 288. However, the number of nipples and detents can be altered so long as there are provided at least three unique stop positions for the handle portion 264.

The latch plate 274 is provided with a circular shape having an arcuate section thereof cut off at 292. However, so long as there are two lateral extending sections to the plate, it should suffice.

The locking mechanism is connected to the upper end of the door panel 22, as best shown in FIG. 1. The lateral extensions of the latch plate 274 are such that they can extend upwardly beneath the distal free end 256 of the skirt portion 254 of the top wall 12. As shown in FIG. 17, one of the lateral sections 294 of latch plate 274 is provided at one end, with another lateral section 296 provided adjacent thereto, the cut off section 292 being thereacross. It should be noted, that a mating nipple and detent is provided for these three positions.

A first position of the locking mechanism is shown in FIG. 17. In this position, the lateral extension 294 extends upwardly beneath the skirt portion 254 so as to prevent the door 22 from being opened. This position is used to indicate that the cart contains sterile equipment and is ready to be brought into the operating room. In this position, the doors are locked and cannot be opened even if the foot latch is accidentally depressed.

Figure 19:
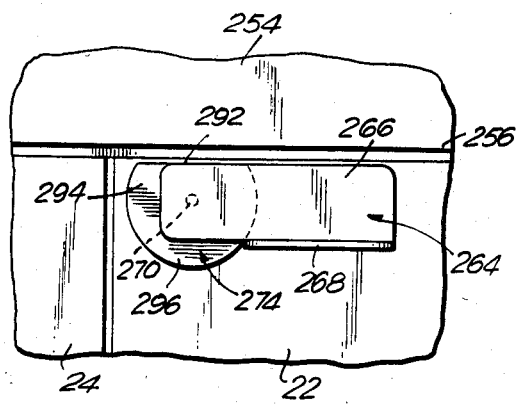
FIG. 19 is a fragmented front view showing the latch mechanism in its open position.

Referring now to FIG. 19, it is noted that the flattened portion 292 of the latch plate 297 faces upwardly with the handle portion 264 lying in a horizontal position toward the right. In this position, the doors are unlocked, whereby the foot latch 136 is operative to open the door. In the position shown in FIG. 20, the handle 264 is now placed in the left hand position, whereby the lateral extension 296 now engages beneath the skirt portion 254 and again prevents the doors from being opened. The locked position shown in FIG. 20, and also in FIG. 1, is the one utilized to show that the contents of the container are in a contaminated condition and ready to be brought into the decontamination area.

It should be appreciated, that in the two locked positions, the foot pedal 136 is ineffective to open the door panels. On the other hand, when the lock is in the open position, as shown in FIG. 19, the foot pedal 136 can be used to automatically open the door.

Figure 20:
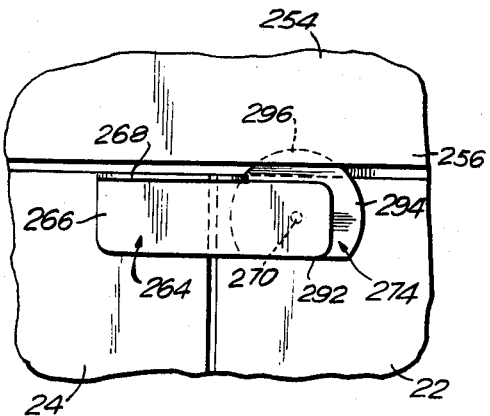
FIG. 20 is a fragmented front view showing the latch mechanism in its other locked position.

The cart normally leaves the supply area with the handle in the position shown in FIG. 17 indicating that the cart has sterile contents. In this position, it will be brought to the operating room area. At that place, inventory is taken prior to the operation and the latch is then left in the open position shown in FIG. 19. In this position, the foot latch 136 can be easily utilized to release the door panels and open the door panels without the use of the operator's hands. At the conclusion of the operation, the contaminated equipment is returned to the cart and the latch is positioned as shown in FIG. 20. Thereagain, the doors are retained closed even in the event of inadvertent activation of the foot pedal 136. The position of the handle portion 264 is here intended to indicate that the cart is now in a contaminated state. However, it is understood, that the indications of the two locked positions can be reversed without any change in the structure of the handle position 264, whereby the position shown in FIG. 17 could just as well mean the contents are contaminated, and the position shown in FIG. 20 would then mean the contents are sterile.

Although the locking mechanism shown in FIGS. 16-20 is only applied to one door panel 22, it will be noted in Figs. 2 and 5 that the adjacent door panel 24 has a U-shaped edge 300 along the abutting edge which closes adjacent to the door panel 22. With the door panels in the closed position, the door panel 24 is closed first, and the door panel 22 is then closed thereon so that the edge 300 is locked beneath the adjacent edge of the door panel 22. Accordingly, with the locking mechanism handle portion 264 locked onto the door panel 22 as shown in FIG. 17, the door panel 24 will automatically be held closed.

At the same time, as is noted in FIG. 5, when the two door panels are in their completely open position, with the front door panels lying over the back wall 16, the door panel 22 is closed onto the back wall 16 first, and the door panel 24 is then closed thereon so that the edge 300 serves to hold the door panel 22 in place. The rear latch 166 then latches onto the lip 124 of the door panel 24 to securely hold both door panels in place.

Figure 21:
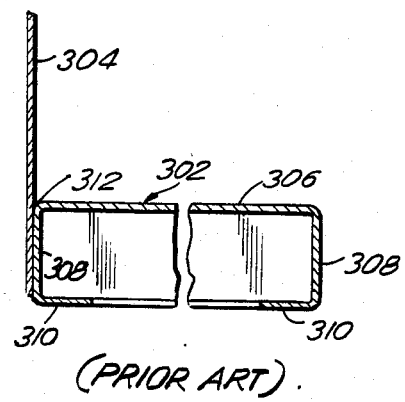
FIG. 21 is a schematic sectional elevational view showing the interconnection between the back wall and the chassis in accordance with prior art surgical case carts.

Referring now to FIG. 21, it is noted that in the prior art carts, there exists an unsanitary condition where the chassis 302 joins the back and/or side wall 304. Typically the chassis is formed to include a top wall 306 with downwardly depending side walls 308 and an inwardly turned lower flange 310. The back and/or side wall is secured onto the vertical side wall 308 by means of welds or other fastening members. However, at the point of intersection 312, a condition is generated where the two pieces of metal are adjacent to one another and where the space is normally not sealed. This problem exists not only in connecting the back wall to the chassis but also the side walls to the chassis. As a result, the space covers a great deal of area around a good portion of the periphery of the cart, and in this large area, bacteria can be retained.

In order to try to reduce this problem, the joint 312 is often filled with sealant material. However, it is generally found that due to the nature of the joint, these sealant materials become dislodged during the cart washing, and the resultant cavity becomes a collection point for dirt and water, and cannot be cleaned properly.

In order to avoid this situation, the present invention contemplates an improved junction which avoids the vertical adjacency of the metal between the walls and the chassis. Specifically, referring now to FIG. 22, there is shown a chassis 314 again having an upper wall 316 with a downwardly depending skirt portion 318 and inwardly turned sloping flanges 320. The back and/or side wall 322 is shown having its lower edge terminating in an inwardly directed flange 324. Typically, this flange 324 is arranged at an angle of 45 degrees from the back wall and/or side wall. The flange edge 326 comes in contact with the chassis upper wall 316 at a point removed from the back of the chassis, and is welded at the edge 326. As a result, there is no surface contact between the back and/or side wall and the chassis, and consequently no harborage area for bacteria. Since continuous welding can be used, there will be no cracks or crevices inside the cart, and at the outside of the cart the joint is opened and exposed to a thorough washing. In this type of construction, the side walls can be made integral with the back wall, and are also joined to the chassis in the same manner as shown in FIG. 22.

Figure 22:
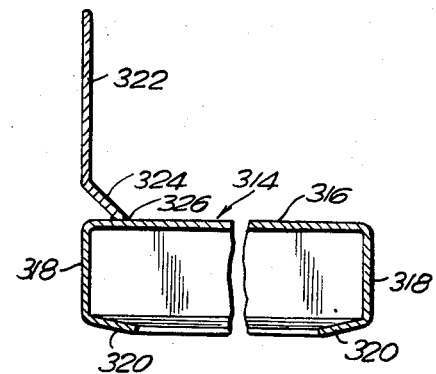
FIG. 22 is a schematic sectional elevational view similar to that shown in FIG. 21, showing a first embodiment of a novel interconnection in accordance with the present invention.
Figure 23:
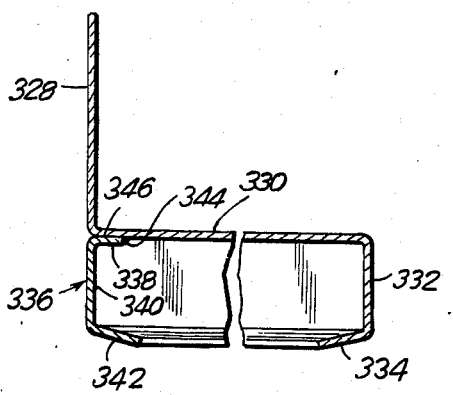
FIG. 23 is a schematic sectional elevational view similar to that shown in FIGS. 21 and 22, showing a second embodiment of interconnecting the back wall with the chassis in accordance with the present invention.

A second embodiment is shown in FIG. 23. In this case, the back and/or side wall 328 is formed integral with the upper wall 330 of the chassis, and continues downward into the front skirt portion 332 and the lower inwardly turned flange 334. The back wall could also be formed integrally with the side walls. The lower end of the side walls would be attached to the chassis utilizing the embodiment shown in FIG. 22, or in that shown in FIG. 24.

The structure shown in FIG. 23, results in an extremely cleanable inside surface in that there is no joint at all at the back. In order to properly support the chassis, a support piece 336 can be attached with the upper horizontal leg 338 secured to the underside of the upper wall 330, and also has a downwardly depending skirt portion 340 similar to the skirt portion 332. There would also be a matching inwardly directed angled flange portion 342 matching that of the flange 334. Although there does result a seam 344 at the interconnection between the leg 338 and the upper wall 330, this seam is outside the cart and does not provide for any contamination. Surface contact along the joint 346 is minimal. Various attachment methods can be utilized including spot welding.

Figure 24:
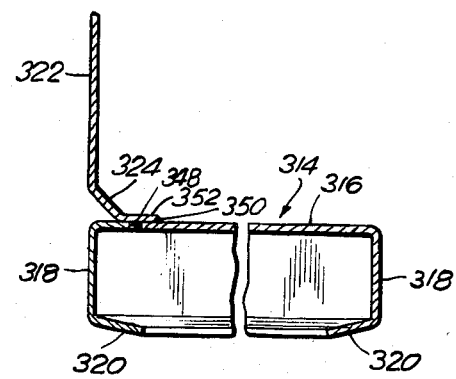
FIG. 24 is a schematic sectional elevational view similar to that shown in FIGS. 21-23, showing yet a third embodiment of such interconnection in accordance with the present invention.

Referring now to FIG. 24, there is shown a variation of the embodiment shown in FIG. 22, where the expensive continuous weld shown at 326 in FIG. 22 has been replaced by a series of spot or plug welds 348, along with a solder seal along the edge 350. In this embodiment, an additional horizontal leg 352 extends from the angled flange 324 and provides for surface contact along the top of the upper wall 316. This leg 352 is the one that is spot welded to the upper wall 316. It is at the front edge 350 thereof where the solder is disposed. The surface contact area is minimal and the inside of the joint is sealed by soldering.

Reliance is not made on the solder for strength, but rather on the plug or spot welds 348. The flat contact leg 352 is only required because of the fact that the welds must be removed from the solder joint so that the oxidation resulting from the welding operation does not interfere with the adhesion of the solder. The side walls of the embodiment shown in FIG. 24 would again be made integral with the back walls and would be joined to the chassis in the same way as shown in FIG. 22, or in accordance with that shown in FIG. 24. It is noted, that the inwardly directed flange 324 is provided on the side walls 28, 32 and the rear wall 16, as shown in FIGS. 1 and 6.

Accordingly, the present invention provides a unique surgical case cart which has improved accessibility through the use of the side door panels to which the front door panels are mounted. This results in increased visability, increased facility for cleaning, and results in the benefits of an open cart while providing the security and sanitary condition of a closed cart. The construction of the chassis is improved in that the casters are stem mounted, and there are no flat horizontal surfaces on which dirt can collect on the casters. Also, the relationship between the back, the sides and the chassis, where the intersection thereof occurs, is made more sanitary than in the prior art. The construction of the door panels is improved, wherein they have no cracks, crevices, or concealed areas. At the same time, the door panels exhibit the rigidity of double pan doors. The edges of the door panels create a full baffle effect in order to reduce the movement of contaminated air into or out of the cart.

The present construction also includes an improved front top edge where liquids spilled on the top wall do not drip into the inside of the container. The door latch provides an improvement since it serves both to retain the door panels as well as indicate whether the cart contents are sterile or contaminated. At the same time, openings of the cart in the operating room can be accomplished without the use of the operator's hands.

There has been described heretofore the best embodiments of the invention presently contemplated. However, it is to be understood that various changes and modifications may be made thereto without departing from the spirit of the invention.

What is claimed is:

1. A cart comprising:

an enclosed container having a pair of adjacent first and second front door panels with an overlying top wall, said top wall having a depending lip;

latching means having two distinguishably different closed positions including a first closed position for locking at least said first front door panel and a second closed position for locking both of said front door panels;

said latching means having an open position for permitting opening of both of said front door panels;

said latching means including a plate member rotatably coupled to said first front door panel;

said plate member having a cut off section and at least first and second laterally extending engagement portions for engaging said top wall lip to prevent opening of said first front door panel;

handle means secured to said plate member for selectively rotating said plate member into one of said closed and open positions;

said handle means extending outwardly from said plate member in a direction parallel to a free edge of said cut off section of said plate member;

said open position being provided when said free edge of said cut off section of said plate member and a longitudinal edge of said handle means extend along said first front door panel and are disposed horizontally adjacent to a top edge of said first front door panel;

said first closed position being provided when said handle means is rotated 90 degrees from said open position so that said first engagement portion of said plate member engages behind said top wall lip; and said second closed position being provided when said handle means is rotated 180 degrees from said open position so that said second engagement portion of said plate member engages behind said top wall lip and said handle means extends in front of said second front door panel to prevent opening of said second front door panel.

2. A cart as in claim 1, wherein said plate member includes at least one nipple and said first front door panel includes detent means for selectively receiving said nipple, and wherein each engaging combination of said nipple and one of said detent means defines one of said closed and open positions, one closed position respectively corresponding to each of said first and second laterally extending engagement portions engaging said lip, and said open position corresponding to a non-engagement of said cut off section relative to said lip.

3. A cart as in claim 1, and further comprising release means releasably engaging at least said first front door panel, activation of said release means permitting the opening of said front door panels when said latching means is in said open position, said release means being ineffective when said latching means is in either of said closed positions.

4. A cart as in claim 1, and further comprising a laterally extending flange along an abutting edge of the second front door panel for positioning behind said first front door panel, whereby said second front door panel is held closed by said first front door panel.

* * * * *